United States Patent
Gaudry et al.

(10) Patent No.: US 9,925,132 B2
(45) Date of Patent: Mar. 27, 2018

(54) FLUID AQUEOUS ANTISUN COMPOSITION BASED ON A SUPERABSORBENT POLYMER AND A CROSSLINKED COPOLYMER OF METHACRYLIC ACID AND OF A C1-C4 ALKYL ACRYLATE

(75) Inventors: Anne-Laure Gaudry, La Ferte Gaucher (FR); Celine Ruzand, Crest (FR)

(73) Assignee: L'OREAL, Paris (FR)

( * ) Notice: Subject to any disclaimer, the term of this patent is extended or adjusted under 35 U.S.C. 154(b) by 843 days.

(21) Appl. No.: 13/882,908

(22) PCT Filed: Oct. 21, 2011

(86) PCT No.: PCT/EP2011/068473
§ 371 (c)(1),
(2), (4) Date: Aug. 20, 2013

(87) PCT Pub. No.: WO2012/059348
PCT Pub. Date: May 10, 2012

(65) Prior Publication Data
US 2014/0030297 A1    Jan. 30, 2014

Related U.S. Application Data

(60) Provisional application No. 61/411,210, filed on Nov. 8, 2010.

(30) Foreign Application Priority Data

Nov. 5, 2010 (FR) ..................... 10 59143

(51) Int. Cl.
| | |
|---|---|
| A61K 8/06 | (2006.01) |
| A61K 8/81 | (2006.01) |
| A61K 8/73 | (2006.01) |
| A61Q 17/04 | (2006.01) |

(52) U.S. Cl.
CPC .................. *A61K 8/81* (2013.01); *A61K 8/06* (2013.01); *A61K 8/062* (2013.01); *A61K 8/731* (2013.01); *A61K 8/732* (2013.01); *A61K 8/737* (2013.01); *A61K 8/8152* (2013.01); *A61Q 17/04* (2013.01); *A61K 2800/412* (2013.01)

(58) Field of Classification Search
CPC ......... A61K 8/152; A61K 8/042; A61K 8/368
See application file for complete search history.

(56) References Cited

U.S. PATENT DOCUMENTS

| | | | |
|---|---|---|---|
| 5,553,630 A | 9/1996 | Dupuis et al. | |
| 5,695,747 A | 12/1997 | Forestier et al. | |
| 2003/0103926 A1* | 6/2003 | Maubru ............... | A61K 8/8152 424/70.12 |
| 2005/0019356 A1* | 1/2005 | Bissett .................. | A61K 8/368 424/401 |
| 2005/0053561 A1 | 3/2005 | Suginaka | |
| 2005/0255134 A1 | 11/2005 | Hasenzahl et al. | |
| 2006/0128902 A1 | 6/2006 | Flohr et al. | |
| 2008/0108534 A1* | 5/2008 | Bernard ................ | A61K 8/042 510/119 |
| 2010/0104520 A1* | 4/2010 | Candau ................. | A61K 8/042 424/59 |
| 2010/0330018 A1 | 12/2010 | Lorant et al. | |
| 2011/0027202 A1 | 2/2011 | Candau et al. | |

FOREIGN PATENT DOCUMENTS

| | | |
|---|---|---|
| EP | 0518773 A1 | 12/1992 |
| EP | 2266531 A1 | 12/2010 |
| FR | 2924930 A1 | 6/2009 |
| JP | 2007-505116 A | 3/2007 |
| JP | 2008-523173 A | 7/2008 |
| WO | WO-2004/105704 A2 | 12/2004 |
| WO | WO-2005/058256 A1 | 6/2005 |
| WO | WO-2006/024768 A2 | 3/2006 |
| WO | WO-2009/080661 A2 | 7/2009 |

OTHER PUBLICATIONS

Japanese Office Action dated Aug. 24, 2015 in JP Application No. 2013-537061.

* cited by examiner

*Primary Examiner* — Micah Paul Young
(74) *Attorney, Agent, or Firm* — Polsinelli PC

(57) ABSTRACT

The present invention relates to a fluid composition, characterized in that it comprises, in a cosmetically acceptable aqueous support:
(a) at least one fatty phase;
(b) a photoprotective system capable of screening out UV radiation;
(c) at least one superabsorbent polymer;
(d) at least one crosslinked copolymer of methacrylic acid and of a $C_1$-$C_4$ alkyl acrylate.

Another subject of the present invention lies in the use of the combination of a superabsorbent polymer and of a crosslinked copolymer of methacrylic acid and of an alkyl acrylate in a fluid composition comprising, in a cosmetically acceptable aqueous support, at least one photoprotective system capable of screening out UV radiation, as a freshness agent and/or as a stabilizer for the composition.

20 Claims, No Drawings

FLUID AQUEOUS ANTISUN COMPOSITION BASED ON A SUPERABSORBENT POLYMER AND A CROSSLINKED COPOLYMER OF METHACRYLIC ACID AND OF A C1-C4 ALKYL ACRYLATE

CROSS REFERENCE TO RELATED APPLICATIONS

This application is a National Phase filing under 35 U.S.C. § 371 of PCT/EP2011/068473 filed on Oct. 21, 2011; and this application claims priority to Application No. 1059143 filed in France on Nov. 5, 2010, and claims the benefit of U.S. Provisional Application 61/411,210 filed on Nov. 8, 2010; the entire contents of all are hereby incorporated by reference.

The present invention relates to a fluid composition, characterized in that it comprises, in a cosmetically acceptable aqueous support:
(a) at least one fatty phase;
(b) a photoprotective system capable of screening out UV radiation;
(c) at least one superabsorbent polymer;
(d) at least one crosslinked copolymer of methacrylic acid and of a $C_1$-$C_4$ alkyl acrylate.

It is known that light radiation with wavelengths of between 280 nm and 400 nm permits tanning of the human epidermis and that light rays with wavelengths between 280 and 320 nm, known as UV-B rays, cause skin burns and erythema which can harm the development of a natural tan; this UV-B radiation should thus be screened out.

It is also known that UV-A rays, with wavelengths between 320 and 400 nm, which cause tanning of the skin, are liable to induce adverse changes therein, in particular in the case of sensitive skin or skin that is continually exposed to solar radiation. UV-A rays cause in particular a loss of elasticity of the skin and the appearance of wrinkles leading to premature ageing of the skin. They promote triggering of the erythemal reaction or amplify this reaction in certain individuals and may even be the cause of phototoxic or photoallergic reactions. It is thus desirable also to screen out UV-A radiation.

Many cosmetic compositions for photoprotecting the skin (against UV-A and/or UV-B) have been proposed to date. Fluid formulations that are easy for the users to apply to the skin are most particularly sought.

These fluid antisun compositions are quite often in the form of an emulsion, of oil-in-water type (i.e. a cosmetically acceptable support consisting of an aqueous dispersing continuous phase and of an oily discontinuous phase), which contains, in varying concentrations, one or more standard lipophilic and/or hydrophilic organic screening agents capable of selectively absorbing the harmful UV radiation, these screening agents (and the amounts thereof) being selected as a function of the desired sun protection factor, the sun protection factor (SPF) being expressed mathematically as the ratio of the dose of UV radiation required to reach the erythema-forming threshold with the UV-screening agent to the dose of the UV radiation required to reach the erythema-forming threshold without the UV-screening agent.

The aqueous fluid formulations currently on the antisun products market do not afford a noteworthy freshness effect. To afford freshness, it is possible to add one or more gelling agents. However, the use of certain mixtures of gelling agents does not make it possible to stabilize the formulation or to maintain its fluidity. This instability may be reflected especially by graining-out or phase separation in the case of an emulsion or a substantial deposit at the bottom of a container such as a tube.

Thus, there is still a need to find a suitable gelling system in fluid aqueous antisun products that are stable on storage and easy to spread, and that afford a noteworthy freshness effect, without the drawbacks mentioned previously.

Now, after considerable research conducted in the above-mentioned field of photoprotection, the Applicant has discovered, surprisingly, that the use of a to combination of a superabsorbent polymer and of a crosslinked copolymer of methacrylic acid and of an alkyl acrylate in a fluid aqueous composition containing at least one system for screening out UV radiation allows this objective to be achieved.

The Applicant has discovered that antisun compositions obtained with this particular combination of polymers produce fluid aqueous formulations that have the following properties:
a creamy, foamy texture
noteworthy freshness on application
persistent freshness after application
a formula that is easy to spread.
This discovery forms the basis of the present invention.

Thus, in accordance with a first subject of the present invention, a fluid composition is proposed, characterized in that it comprises, in a cosmetically acceptable aqueous support:
(a) at least one fatty phase;
(b) a photoprotective system capable of screening out UV radiation;
(c) at least one superabsorbent polymer;
(d) at least one crosslinked copolymer of methacrylic acid and of a $C_1$-$C_4$ alkyl acrylate.

According to the invention, the term "photoprotective system capable of screening out UV radiation" is generally intended to denote any compound or any combination of compounds which, via mechanisms that are known per se for the absorption and/or reflection and/or scattering of UV-A and/or UV-B radiation, can prevent, or at least limit, the contact of the said radiation with a surface (skin, hair) onto which this or these compounds have been applied. In other words, these compounds may be UV-absorbing photoprotective organic screening agents or UV-scattering and/or UV-reflecting mineral pigments, and also mixtures thereof.

The term "cosmetically acceptable" means compatible with the skin and/or its integuments, which has a pleasant colour, odour and feel, and which does not cause any unacceptable discomfort (stinging, tautness or redness) liable to put the consumer off using this composition.

For the purposes of the invention, the term "fluid composition" means a composition that is not in solid form and whose viscosity, measured using a Rheomat 180 viscometer at 25° C. at a spin speed of 200 rpm after 10 minutes of rotation, is less than or equal to 2 Pa·s, preferably ranging from 0.3 to 1.6 Pa·s and more particularly from 0.5 Pa·s to 1.5 Pa·s.

Another subject of the present invention lies in the use of the combination of a superabsorbent polymer and of a crosslinked copolymer of methacrylic acid and of an alkyl acrylate in a fluid composition comprising, in a cosmetically acceptable aqueous support, at least one photoprotective system capable of screening out UV radiation, as a freshness agent and/or as a stabilizer for the composition.

Other characteristics, aspects and advantages of the present invention will emerge on reading the detailed description that follows.

Superabsorbent Polymer

The term "superabsorbent polymer" means a polymer that is capable in its dry form of spontaneously absorbing at least 20 times its own weight of aqueous fluid, in particular of water and especially distilled water. Such superabsorbent polymers are described in the publication "Absorbent polymer technology, Studies in polymer science 8" by L. Brannon-Pappas and R. Harland, published by Elsevier, 1990.

These polymers have a large capacity for absorbing and retaining water and aqueous fluids. After absorption of the aqueous liquid, the polymer particles thus engorged with aqueous fluid remain insoluble in the aqueous fluid and thus conserve their individualized particulate state.

The superabsorbent polymer may have a water-absorbing capacity ranging from 20 to 2000 times its own weight (i.e. 20 g to 2000 g of absorbed water per gram of absorbent polymer), preferably from 30 to 1500 times and better still from 50 to 1000 times. These water absorption characteristics are defined under standard temperature (25° C.) and pressure (760 mmHg, i.e. 100 000 Pa) conditions and for distilled water.

The value of the water-absorbing capacity of a polymer may be determined by dispersing 0.5 g of polymer(s) in 150 g of a water solution, waiting for 20 minutes, filtering the unabsorbed solution through a 150 µm filter for 20 minutes and weighing the unabsorbed water.

The superabsorbent polymer used in the composition of the invention is in the form of particles, which, once hydrated, swell to form soft beads with a number-average diameter of from 10 µm to 1000 µm.

Preferably, the superabsorbent polymer has a number-average size of less than or equal to 100 µm and preferably less than or equal to 50 µm, for example ranging from 10 to 100 µm.

Preferably, the superabsorbent polymers used in the present invention are in the form of spherical particles.

The superabsorbent polymers used in the present invention are preferably crosslinked acrylic homopolymers or copolymers, which are preferably neutralized, and which are in particulate form.

Mention may be made especially of absorbent polymers chosen from:

- crosslinked sodium polyacrylates, for instance those sold under the brand names Octacare X100, X110 and RM100 by the company Avecia, those sold under the names Flocare GB300 and Flosorb 500 by the company SNF, those sold under the names Luquasorb 1003, Luquasorb 1010, Luquasorb 1280 and Luquasorb 1110 by the company BASF, those sold under the names Water Lock G400 and G430 (INCI name: Acrylamide/sodium acrylate copolymer) by the company Grain Processing, or Aqua Keep 10 SH NF (INCI name: Sodium Acrylates Crosspolymer-2 (and) Aqua (and) Silica) sold by the company Sumitomo Seika,
- starches grafted with an acrylic polymer (homopolymer or copolymer) and especially with sodium polyacrylate, such as those sold under the names Sanfresh ST-100C, ST100MC and IM-300MC by the company Sanyo Chemical Industries (INCI name: Sodium polyacrylate starch),
- hydrolysed starches grafted with an acrylic polymer (homopolymer or copolymer) and especially acryloacrylamide/sodium acrylate copolymer, such as those sold under the names Water Lock A-240, A-180, B-204, D-223, A-100, C-200 and D-223 by the company Grain Processing (INCI name: Starch/acrylamidelsodium acrylate copolymer),
- polymers based on starch, gum and cellulose derivative, such as the product containing starch, guar gum and sodium carboxymethylcellulose, sold under the name Lysorb 220 by the company Lysac,
- and mixtures thereof.

Preferably, the superabsorbent polymer is chosen from crosslinked sodium polyacrylates, preferably in the form of particles with a number-average size (or mean diameter) of less than or equal to 100 microns, more preferably in the form of spherical particles. These polymers preferably have a water-absorbing capacity from 10 to 100 g/g, preferably from 20 to 80 g/g and better still from 50 to 70 g/g.

The superabsorbent polymer may be present in the composition of the invention in an active material content ranging, for example, from 0.1% to 2% by weight, preferentially ranging from 0.5% to 1.5% by weight and more particularly from 0.5% to 1% by weight relative to the total weight of the composition.

Crosslinked Copolymer of Methacrylic Acid and of a C1-C4 Alkyl Acrylate

One of the essential characteristics of the invention is the presence of a crosslinked copolymer of methacrylic acid and of a C1-C4 alkyl acrylate.

Methacrylic acid is preferably present in amounts ranging from 20% to 80% by weight, more particularly from 25% to 70% by weight and even more particularly from 35% to 65% by weight relative to the total weight of the copolymer.

The alkyl acrylate is preferably present in amounts ranging from 15% to 80% by weight, more particularly from 25% to 75% by weight and even more particularly from 35% to 65% by weight relative to the total weight of the copolymer. It is chosen especially from methyl acrylate, ethyl acrylate and butyl acrylate and more particularly ethyl acrylate.

This copolymer is preferably partially or totally crosslinked with at least one standard polyethylenically unsaturated crosslinking agent, for instance polyalkenyl ethers of sucrose or of polyols, diallyl phthalates, divinylbenzene, allyl (meth)acrylate, ethylene glycol di(meth)acrylate, methylenebisacrylamide, trimethyloipropane tri(meth)acrylate, diallyl itaconate, diallyl fumarate, diallyl maleate, zinc (meth)acrylate, and castor oil or polyol derivatives manufactured from unsaturated carboxylic acids. The content of crosslinking agent generally ranges from 0.01% to 5% by weight, preferably from 0.03% to 3% by weight and even more particularly from 0.05% to 1% by weight relative to the total weight of the copolymer.

According to one particularly preferred form, the copolymer of the invention may especially be in the form of a dispersion in water. The mean size of the copolymer particles in the dispersion is generally between 10 and 500 nm, preferably between 20 and 200 nm and more preferentially from 50 to 150 nm.

Mention may be made in particular of the methacrylic acid/ethyl acrylate crosslinked copolymer sold by the company Noveon under the trade name Carbopol Aqua SF1.

The copolymer concentration preferably ranges from 0.01% to 1% by weight of active material relative to the total weight of the composition, preferably from 0.1% to 0.6% by weight of active material relative to the total weight of the composition and preferably from 0.15% to 0.3% by weight of active material relative to the total weight of the composition.

Photoprotective System

According to the invention, the photoprotective system may be formed from one or more hydrophilic, lipophilic or insoluble organic screening agents and/or one or more mineral pigments. It will preferentially be formed from at least one hydrophilic, lipophilic or insoluble organic UV-screening agent.

The organic UV-screening agents are chosen especially from cinnamic derivatives; anthranilates; salicylic derivatives; dibenzoylmethane derivatives, camphor derivatives; benzophenone derivatives; β,β-diphenylacrylate derivatives; triazine derivatives; benzotriazole derivatives; benzalmalonate derivatives, especially those mentioned in U.S. Pat. No. 5,624,663; benzimidazole derivatives; imidazolines; bis-benzazolyl derivatives as described in patents EP 669 323 and U.S. Pat. No. 2,463,264; p-aminobenzoic acid (PABA) derivatives; methylenebis(hydroxyphenylbenzotriazole) derivatives as described in patent applications U.S. Pat. Nos. 5,237,071, 5,166,355, GB 2 303 549, DE 197 26 184 and EP 893 119; benzoxazole derivatives as described in patent applications EP 0 832 642, EP 1 027 883, EP 1 300 137 and DE 101 62 844; screening polymers and screening silicones such as those described especially in patent application WO 93/04665; α-alkylstyrene-based dimers, such as those described in patent application DE 198 55 649; 4,4-diarylbutadienes such as those described in patent applications EP 0 967 200, DE 197 46 654, DE 197 55 649, EP-A-1 008 586, EP 1 133 980 and EP 133 981; merocyanin derivatives such as those described in patent applications WO 04/006 878, WO 05/058 269 and WO 06/032 741; and mixtures thereof.

As examples of additional organic photoprotective agents, mention may be made of those denoted hereinbelow under their INCI name:

Cinnamic Derivatives:
Ethylhexyl methoxycinnamate sold in particular under the trade name Parsol MCX by Hoffmann LaRoche,
Isopropyl methoxycinnamate,
Isoamyl methoxycinnamate sold under the trade name Neo Heliopan E 1000 by Haarmann & Reimer,
DEA Methoxycinnamate,
Diisopropyl methylcinnamate,
Glyceryl ethylhexanoate dimethoxycinnamate Dibenzoylmethane Derivatives:
Butylmethoxydibenzoylmethane sold especially under the trade name Parsol 1789 by Hoffmann LaRoche,
Isopropyldibenzoylmethane.

para-Aminobenzoic Acid Derivatives:
PABA,
Ethyl PABA,
Ethyl dihydroxypropyl PABA,
Ethylhexyl dimethyl PABA sold in particular under the name Escalol 507 by ISP,
Glyceryl PABA,
PEG-25 PABA sold under the name Uvinul P25 by BASF, Salicylic Derivatives:
Homosalate sold under the name Eusolex HMS by Rona/EM Industries,
Ethylhexyl salicylate sold under the name Neo Heliopan OS by Haarmann and Reimer,
Dipropylene glycol salicylate sold under the name Dipsal by Scher,
TEA salicylate sold under the name Neo Heliopan TS by Haarmann & Reimer, β,β-Diphenylacrylate Derivatives:
Octocrylene sold especially under the trade name Uvinul N539 by BASF,
Etocrylene sold especially under the trade name Uvinul N35 by BASF, Benzophenone Derivatives:
Benzophenone-1 sold under the trade name Uvinul 400 by BASF,
Benzophenone-2 sold under the trade name Uvinul D50 by BASF,
Benzophenone-3 or oxybenzone sold under the trade name Uvinul M40 by BASF,
Benzophenone-4 sold under the trade name Uvinul MS40 by BASF,
Benzophenone-5,
Benzophenone-6 sold under the trade name Helisorb 11 by Norquay,
Benzophenone-8 sold under the trade name Spectra-Sorb UV-24 by American Cyanamid,
Benzophenone-9 sold under the trade name Uvinul DS-49 by BASF,
Benzophenone-12,
n-hexyl 2-(4-diethylamino-2-hydroxybenzoyl)benzoate sold under the trade name Uvinul A+, or in the form of a mixture with octyl methoxycinnamate under the trade name Uvinul A+B by the company BASF.

Benzylidenecamphor Derivatives:
3-Benzylidenecamphor manufactured under the name Mexoryl SD by Chimex,
4-Methylbenzylidenecamphor sold under the name Eusolex 6300 by Merck,
Benzylidenecamphorsulfonic acid manufactured under the name Mexoryl SL by Chimex,
Camphor benzalkonium methosulfate manufactured under the name Mexoryl SO by Chimex,
Terephthalylidenedicamphorsulfonic acid manufactured under the name Mexoryl SX by Chimex,
Polyacrylamidomethylbenzylidenecamphor manufactured under the name Mexoryl SW by Chimex, Phenylbenzimidazole Derivatives:
Phenylbenzimidazolesulfonic acid sold in particular under the trade name Eusolex 232 by Merck,
Disodium phenyl dibenzimidazole tetrasulfonate sold under the trade name Neo Heliopan AP by Haarmann and Reimer.

Phenylbenzotriazole Derivatives:
Drometrizole trisiloxane sold under the name Silatrizole by Rhodia Chimie,
Methylenebis(benzotriazolyl)tetramethylbutylphenol sold in solid form under the trade name Mixxim BB/100 by Fairmount Chemical, or in micronized form as an aqueous dispersion under the trade name Tinosorb M by Ciba Specialty Chemicals.

Triazine Derivatives:
Bis(ethylhexyloxyphenol)methoxyphenyltriazine sold under the trade name Tinosorb S by Ciba Geigy,
Ethylhexyltriazone sold in particular under the trade name Uvinul T150 by BASF,
Diethylhexylbutamidotriazone sold under the trade name Uvasorb HEB by Sigma 3V,
2,4,6-tris(dineopentyl 4'-aminobenzalmalonate)-s-triazine
2,4,6-tris(diisobutyl 4'-aminobenzalmalonate)-s-triazine,
2,4-bis(n-butyl 4'-aminobenzoate)-6-(aminopropyltrisiloxane)-s-triazine,
2,4-bis(dineopentyl 4'-aminobenzalmalonate)-6-(n-butyl 4'-aminobenzoate)-s-triazine,
the symmetrical triazine screening agents described in U.S. Pat. No. 6,225,467, patent application WO 2004/085 412 (see compounds 6 and 9) or the document Symmetrical Triazine Derivatives IP.COM Journal, IP.COM INC West Henrietta, N.Y., US (20 Sep. 2004), especially 2,4,6-tris (biphenyl)-1,3,5-triazines (in particular 2,4,6-tris(biphenyl-4-yl-1,3,5-triazine) and 2,4,6-tris(terphenyl)-1,3,5-triazine which is also mentioned in patent applications WO 06/035 000, WO 06/034 982, WO 06/034 991, WO 06/035 007, WO 2006/034 992 and WO 2006/034 985).

Anthranilic Derivatives:
Menthyl anthranilate sold under the trade name Neo Heliopan MA by Haarmann and Reimer.

Imidazoline Derivatives:
Ethylhexyldimethoxybenzylidenedioxoimidazoline propionate, Benzalmalonate Derivatives:
Polyorganosiloxane containing benzalmalonate functions, for instance Polysilicone-15, sold under the trade name Parsol SLX by Hoffmann LaRoche 4,4-Diarylbutadiene Derivatives:
1,1-Dicarboxy(2,2'-dimethylpropyl)-4,4-diphenylbutadiene.

Benzoxazole Derivatives:
2,4-Bis(5-[(dimethylpropyl)benzoxazol-2-yl-(4-phenyl)imino]-6-(2-ethylhexyl)imino-1,3,5-triazine, sold under the name of Uvasorb K2A by Sigma 3V,
and mixtures thereof.

The preferential organic screening agents are chosen from:
Ethylhexyl methoxycinnamate,
Ethylhexyl salicylate,
Homosalate,
Butylmethoxydibenzoylmethane,
Octocrylene,
Phenylbenzimidazolesulfonic acid,
Benzophenone-3,
Benzophenone-4,
Benzophenone-5,
n-Hexyl 2-(4-diethylamino-2-hydroxybenzoyl)-benzoate.
4-Methylbenzylidenecamphor,
Terephthalylidenedicamphorsulfonic acid,
Disodium phenyldibenzimidazoletetrasulfonate,
Methylenebis(benzotriazolyl)tetramethylbutyl-phenol,
Bis(ethylhexyloxyphenol)methoxyphenyltriazine,
Ethylhexyl triazone,
Diethylhexylbutamidotriazone,
2,4,6-Tris(dineopentyl 4'-aminobenzalmalonate)-s-triazine,
2,4,6-Tris(diisobutyl 4'-aminobenzalmalonate)-s-triazine,
2,4-Bis(n-butyl 4'-aminobenzoate)-6-(aminopropyltrisiloxane)-s-triazine,
2,4-Bis(dineopentyl 4'-aminobenzalmalonate)-6-(n-butyl 4'-aminobenzoate)-s-triazine,
2,4,6-Tris(biphenyl-4-yl)-1,3,5-triazine,
2,4,6-Tris(terphenyl)-1,3,5-triazine,
Drometrizole trisiloxane,
Polysilicone-15,
1,1-Dicarboxy(2,2'-dimethylpropyl)-4,4-diphenylbutadiene,
2,4-Bis(5-[(dimethylpropyl)benzoxazol-2-yl-(4-phenyl)imino]-6-(2-ethylhexyl)imino-1,3,5-triazine,
and mixtures thereof.

The mineral UV-screening agents used in accordance with the present invention are metal oxide pigments. More preferentially, the mineral UV-screening agents of the invention are metal oxide pigments with a mean elemental particle size of less than or equal to 500 nm, more preferentially between 5 nm and 500 nm and even more preferentially between 10 nm and 100 nm, and preferentially between 15 and 50 nm.

They may be chosen especially from titanium oxide, zinc oxide, iron oxide, zirconium oxide and cerium oxide, or mixtures thereof.

Such coated or uncoated metal oxide pigments are described in particular in patent application EP-A-0 518 773. Commercial pigments that may be mentioned include the products sold by the companies Kemira, Tayca, Merck and Degussa.

The metal oxide pigments may be coated or uncoated.

The coated pigments are pigments that have undergone one or more surface treatments of chemical, electronic, mechanochemical and/or mechanical nature with compounds such as amino acids, beeswax, fatty acids, fatty alcohols, anionic surfactants, lecithins, sodium, potassium, zinc, iron or aluminium salts of fatty acids, metal alkoxides (of titanium or aluminium) of polyethylene, silicones, proteins (collagen, elastin), alkanolamines, silicon oxides, metal oxides or sodium hexametaphosphate.

The coated pigments are more particularly titanium oxides that have been coated:
with silica, such as the product Sunveil from the company Ikeda,
with silica and iron oxide, such as the product Sunveil F from the company Ikeda,
with silica and alumina, such as the products Microtitanium Dioxide MT 500 SA and Microtitanium Dioxide MT 100 SA from the company Tayca and Tioveil from the company Tioxide,
with alumina, such as the products Tipaque TTO-55 (B) and Tipaque TTO-55 (A) from the company Ishihara and UVT 14/4 from the company Kemira,
with alumina and aluminium stearate, such as the product Microtitanium Dioxide MT 100 T, MT 100 TX, MT 100 Z and MT-01 from the company Tayca, the products Solaveil CT-10 W and Solaveil CT 100 from the company Uniqema and the product Eusolex T-AVO from the company Merck,
with silica, alumina and alginic acid, such as the product MT-100 AQ from the company Tayca,
with alumina and aluminium laurate, such as the product Microtitanium Dioxide MT 100 S from the company Tayca,
with iron oxide and iron stearate, such as the product Microtitanium Dioxide MT 100 F from the company Tayca,
with zinc oxide and zinc stearate, such as the product BR351 from the company Tayca,
with silica and alumina and treated with a silicone, such as the products Microtitanium Dioxide MT 600 SAS, Microtitanium Dioxide MT 500 SAS or Microtitanium Dioxide MT 100 SAS from the company Tayca,
with silica, alumina and aluminium stearate and treated with a silicone, such as the product STT-30-DS from the company Titan Kogyo,
with silica and treated with a silicone, such as the product UV-Titan X 195 from the company Kemira,
with alumina and treated with a silicone, such as the products Tipaque TTO-55 (S) from the company Ishihara or UV Titan M 262 from the company Kemira,
with triethanolamine, such as the product STT-65-S from the company Titan Kogyo,
with stearic acid, such as the product Tipaque TTO-55 (C) from the company Ishihara,
with sodium hexametaphosphate, such as the product Microtitanium Dioxide MT 150 W from the company Tayca.
$TiO_2$ treated with octyltrimethylsilane, sold under the trade name T 805 by the company Degussa Silices,
$TiO_2$ treated with a polydimethylsiloxane, sold under the trade name 70250 Cardre UF TiO2SI3 by the company Cardre, anatase/rutile TiO$_2$ treated with a polydimethylhydrogenosiloxane, sold under the trade name Microtitanium Dioxide USP Grade Hydrophobic by the company Color Techniques.

The uncoated titanium oxide pigments are sold, for example, by the company Tayca under the trade names Microtitanium Dioxide MT 500 B or Microtitanium Dioxide MT 600 B, by the company Degussa under the name P 25, by the company Wacker under the name Transparent titanium oxide PW, by the company Miyoshi Kasei under the name UFTR, by the company Tomen under the name ITS and by the company Tioxide under the name Tioveil AQ.

The uncoated zinc oxide pigments are, for example:
those sold under the name Z-Cote by the company Sunsmart;
those sold under the name Nanox by the company Elementis;
those sold under the name Nanogard WCD 2025 by the company Nanophase Technologies.

The coated zinc oxide pigments are, for example:
those sold under the name Zinc Oxide CS-5 by the company Toshibi (ZnO coated with polymethylhydrogenosiloxane);
those sold under the name Nanogard Zinc Oxide FN by the company Nanophase Technologies (as a 40% dispersion in Finsolv TN, C12-C15 alkyl benzoate);
those sold under the name Daitopersion ZN-30 and Daitopersion ZN-50 by the company Daito (dispersions in cyclopolymethylsiloxane/oxyethylenated polydimethylsiloxane, containing 30% or 50% of nanozinc oxides coated with silica and polymethylhydrogenosiloxane);
those sold under the name NFD Ultrafine ZnO by the company Daikin (ZnO coated with perfluoroalkyl phosphate and copolymer based on perfluoroalkylethyl as a dispersion in cyclopentasiloxane);
those sold under the name SPD-ZI by the company Shin-Etsu (ZnO coated with silicone-grafted acrylic polymer, dispersed in cyclodimethylsiloxane);
those sold under the name Escalol Z100 by the company ISP (alumina-treated ZnO dispersed in an ethylhexyl methoxycinnamate/PVP-hexadecene/methicone copolymer mixture);
those sold under the name Fuji ZnO-SMS-10 by the company Fuji Pigment (ZnO coated with silica and polymethylsilsesquioxane);
those sold under the name Nanox Gel TN by the company Elementis (ZnO dispersed at a concentration of 55% in C12-C15 alkyl benzoate with hydroxystearic acid polycondensate).

The uncoated cerium oxide pigments are sold under the name Colloidal Cerium Oxide by the company Rhone-Poulenc.

The uncoated iron oxide nanopigments are sold, for example, by the company Amaud under the names Nanogard WCD 2002 (FE 45b), Nanogard Iron FE 45 BL AQ, Nanogard FE 45R AQ and Nanogard WCD 2006 (FE 45R) or by the company Mitsubishi under the name TY-220.

The coated iron oxide pigments are sold, for example, by the company Amaud under the names Nanogard WCD 2008 (FE 45B FN), Nanogard WCD 2009 (FE 45B 556), Nanogard FE 45 BL 345 and Nanogard FE 45 BL or by the company BASF under the name Transparent Iron Oxide.

Mention may also be made of mixtures of metal oxides, especially of titanium dioxide and of cerium dioxide, including the silica-coated equal-weight mixture of titanium dioxide and of cerium dioxide, sold by the company Ikeda under the name Sunveil A, and also the alumina, silica and silicone-coated mixture of titanium dioxide and of zinc dioxide, such as the product M 261 sold by the company Kemira, or the alumina, silica and glycerol-coated mixture of titanium dioxide and of zinc dioxide, such as the product M 211 sold by the company Kemira.

According to the invention, coated or uncoated titanium oxide pigments are particularly preferred.

The photoprotective system according to the invention is preferably present in the compositions according to the invention in a content ranging from 0.1% to 40% by weight and in particular from 5% to 25% by weight relative to the total weight of the composition.

Fatty Phase

The fatty phase of the compositions of the invention comprises at least one fatty substance and preferably at least one oil.

The fatty substances may be formed from an oil or a wax other than the apolar waxes as defined above, or mixtures thereof. The term oil means a compound that liquid at room temperature. The term wax means a compound that is solid or substantially solid at room temperature and whose melting point is generally greater than 35° C.

When the compositions of the invention are oil-in-water emulsions, the proportion of the fatty phase is preferably from 5% to 50% by weight and more preferably from 10% to 40% by weight relative to the total weight of the composition.

When the compositions of the invention are water-in-oil emulsions, the proportion of the fatty phase is preferably from 30% to 70% and preferentially from 40% to 60% for an inverse emulsion.

As oils that may be present in the fatty phase of the compositions of the invention, mention may be made of mineral oils (paraffin); plant oils (sweet almond oil, macadamia oil, blackcurrant pip oil or jojoba oil); fatty alcohols, fatty amides (such as isopropyl lauroyl sarcosinate sold under the name Eldew SL-205 by the company Ajinomoto), fatty acids or esters (for instance the $C_{12}$-$C_{15}$ alkyl benzoate sold under the trade name Finsolv TN or Witconol TN by the company Witco isopropyl lanolate, triglycerides, including capric/caprylic acid triglycerides, the dicaprylyl carbonate sold under the name Cetiol CC by the company Cognis), oxyethylenated or oxypropylenated fatty esters and ethers; silicone oils (cyclomethicone or polydimethylsiloxanes (PDMS)), fluoro oils and polyalkylenes.

Waxy compounds that may be mentioned include carnauba wax, beeswax, hydrogenated castor oil, polyethylene waxes and polymethylene waxes, for instance the product sold under the name Cirebelle 303 by the company Sasol.

Additives

The aqueous compositions in accordance with the present invention may also comprise standard cosmetic adjuvants chosen especially from organic solvents, ionic or nonionic, hydrophilic or lipophilic thickeners, softeners, humectants, opacifiers, stabilizers, emollients, silicones, antifoams, fragrances, preserving agents, anionic, cationic, nonionic, zwitterionic or amphoteric surfactants, active agents, fillers, polymers, propellants, acidifying or basifying agents or any other ingredient usually used in cosmetics and/or dermatology.

Among the organic solvents that may be mentioned are lower alcohols and polyols. These polyols may be chosen from glycols and glycol ethers, for instance ethylene glycol, propylene glycol, butylene glycol, dipropylene glycol or diethylene glycol.

Hydrophilic thickeners that may be mentioned include carboxyvinyl polymers such as the Carbopol products (carbomers) and the Pemulen products (acrylate/$C_{10}$-$C_{30}$-alkylacrylate copolymer); polyacrylamides, for instance the crosslinked copolymers sold under the names Sepigel 305 (CTFA name: polyacrylamide/$C_{13-14}$ isoparaffin/Laureth 7) or Simulgel 600 (CTFA name: acrylamide/sodium acryloyldimethyllaurate copolymer/isohexadecane/polysorbate 80) by the company SEPPIC; 2-acrylamido-2-methylpropanesulfonic acid polymers and copolymers, optionally crosslinked and/or neutralized, for instance poly(2-acrylamido-2-methylpropanesulfonic acid) sold by the company Hoechst under the trade name Hostacerin AMPS (CTFA name: ammonium polyacryloyldimethyl taurate or Simulgel 800 sold by the company SEPPIC(CTFA name: sodium polyacryolyldimethyltaurate/polysorbate 80/sorbitan oleate); copolymers of 2-acrylamido-2-methylpropanesulfonic acid and of hydroxyethyl acrylate, for instance Simulgel NS and Sepinov EMT 10 sold by the company SEPPIC; cellulose derivatives such as hydroxyethyl cellulose; polysaccharides and especially gums such as xanthan gum; and mixtures thereof.

Lipophilic thickeners that may be mentioned include synthetic polymers such as poly($C_{10}$-$C_{30}$ alkyl acrylates) sold under the name Intelimer IPA 13-1 and Intelimer IPA 13-6 by the company Landec, or modified clays such as hectorite and its derivatives, for instance the products sold under the name Bentone.

Needless to say, a person skilled in the art will take care to select the optional additional compound(s) mentioned above and/or the amounts thereof such that the advantageous properties intrinsically associated with the compositions in accordance with the invention are not, or are not substantially, adversely affected by the envisaged addition(s).

The compositions according to the invention may be prepared according to the techniques that are well known to those skilled in the art. They may in particular be in the form of a simple or complex emulsion (O/W, W/O, O/W/O or W/O/W) such as a milk; in the form of a lotion. They may optionally be packaged as an aerosol and may be in the form of a spray.

The compositions according to the invention are preferably in the form of an oil-in-water or water-in-oil emulsion, more particularly oil-in-water emulsions.

The emulsions generally contain at least one emulsifier chosen from amphoteric, anionic, cationic and nonionic emulsifiers, used alone or as a mixture. The emulsifiers are appropriately chosen according to the emulsion to be obtained (W/O or O/W). The emulsions may also contain stabilizers of other types, for instance fillers, or gelling or thickening polymers.

As emulsifying surfactants that may be used for the preparation of the W/O emulsions, examples that may be mentioned include sorbitan, glycerol or sugar alkyl esters or ethers; silicone surfactants, for instance dimethicone copolyols, such as the mixture of cyclomethicone and of dimethicone copolyol, sold under the name DC 5225 C by the company Dow Corning, and alkyldimethicone copolyols such as laurylmethicone copolyol sold under the name Dow Corning 5200 Formulation Aid by the company Dow Corning; cetyldimethicone copolyol, such as the product sold under the name Abil EM 90R by the company Goldschmidt, and the mixture of cetyldimethicone copolyol, of polyglyceryl isostearate (4 mol) and of hexyl laurate, sold under the name Abil WE O9 by the company Goldschmidt. One or more co-emulsifiers may also be added thereto, which may be chosen advantageously from the group comprising polyol alkyl esters.

Polyol alkyl esters that may especially be mentioned include polyethylene glycol esters, for instance PEG-30 dipolyhydroxystearate, such as the product sold under the name Aracel P135 by the company ICI.

Glycerol and/or sorbitan esters that may especially be mentioned include, for example, polyglyceryl isostearate, such as the product sold under the name Isolan GI 34 by the company Goldschmidt, sorbitan isostearate, such as the product sold under the name Ariacel 987 by the company ICI, sorbitan glyceryl isostearate, such as the product sold under the name Arlacel 986 by the company ICI, and mixtures thereof.

For the O/W emulsions, examples of emulsifiers that may be mentioned include nonionic emulsifiers such as oxyalkylenated (more particularly polyoxyethylenated) fatty acid esters of glycerol; oxyalkylenated fatty acid esters of sorbitan; oxyalkylenated (oxyethylenated and/or oxypropylenated) fatty acid esters, for instance the mixture PEG-100 stearate/glyceryl stearate sold, for example, by the company ICI under the name Arlacel 165; oxyalkylenated (oxyethylenated and/or oxypropylenated) fatty alkyl ethers; sugar esters, for instance sucrose stearate; fatty alkyl ethers of sugars, especially alkyl polyglucosides (APG) such as decylglucoside and laurylglucoside sold, for example, by the company Henkel under the respective names Plantaren 2000 and Plantaren 1200, cetostearyl glucoside optionally as a mixture with cetostearyl alcohol, sold, for example, under the name Montanov 68 by the company SEPPIC, under the name Tegocare CG90 by the company Goldschmidt and under the name Emulgade KE3302 by the company Henkel, and also arachidyl glucoside, for example in the form of a mixture of arachidyl alcohol, behenyl alcohol and arachidyl glucoside, sold under the name Montanov 202 by the company SEPPIC. According to one particular so embodiment of the invention, the mixture of the alkyl polyglucoside as defined above with the corresponding fatty alcohol can be in the form of a self-emulsifying composition, for example as disclosed in the document WO-A-92/06778.

According to one particular embodiment, the composition comprises at least one emulsifier chosen from hydrophobic modified inulins.

According to the invention, the term "hydrophobic modified inulin" especially means an inulin modified with hydrophobic chains, in particular modified by grafting hydrophobic chains onto the hydrophilic backbone of the said inulin.

Inulin belongs to the family of essentially linear fructans whose fructose units are for the majority linked via β-2-1 bonds.

Inulin may be obtained, for example, from chicory, dahlia or Jerusalem artichoke. Preferably, the inulin used in the composition according to the invention is obtained, for example, from chicory.

The inulins used in the compositions according to the invention are hydrophobic-modified. In particular, they are obtained by grafting hydrophobic chains onto the hydrophilic backbone of the fructan.

The hydrophobic chains that may be grafted onto the main chain of the fructan may especially be linear or branched, saturated or unsaturated hydrocarbon-based chains containing from 1 to 50 carbon atoms, such as alkyl, arylalkyl, alkylaryl or alkylene groups; divalent cycloaliphatic groups or organopolysiloxane chains. These hydrocarbon-based or organopolysiloxane chains may especially comprise one or more ester, amide, urethane, carbamate, thiocarbamate, urea, thiourea and/or sulfonamide functions especially such as methylenedicyclohexyl and isophorone; or divalent aromatic groups such as phenylene.

In particular, the inulin has a degree of polymerization from 2 to about 1000 and preferably from 2 to about 60, and a degree of substitution of less than 2 on the basis of a fructose unit.

According to one preferred embodiment, the hydrophobic chains contain at least one alkyl carbamate of formula R—NH—CO— in which R is an alkyl group containing from 1 to 22 carbon atoms.

According to a more preferred embodiment, the hydrophobic chains are lauryl carbamate groups.

In particular, as non-limiting illustrations of hydrophobic modified inulins that may be used in the compositions, mention may be made of stearoyl inulin, such as those sold under the names Lifidrem INST by the company Engelhard and Rheopeart INS by the company Ciba; palmitoyl inulin; undecylenoyl inulin, such as those sold under the names Lifidrem INUK and Lifidrem INUM by the company Engelhard; and inulin lauryl carbamate, such as the product sold under the name Inutec SP1 by the company Orafti.

In particular, an inulin grafted with lauryl carbamate is used, which is derived especially from the reaction of lauryl isocyanate with an inulin, in particular derived from chicory. Examples of these compounds that may especially be mentioned include the product sold under the name Inutec SP1 by the company Orafti.

The content of hydrophobic modified inulin in the composition of the invention may range from 0.01% to 20% by weight, preferably from 0.01% to 10% by weight, preferably from 0.05% to 10% by weight, in particular from 0.1% to 10% by weight, preferably from 0.1% to 5% by weight and even more preferentially from 0.1% to 1% by weight (of active material) relative to the total weight of the said composition.

According to one particular embodiment, the composition comprises at least one emulsifier chosen from "gemini surfactants" comprising two identical or different surfactant units, each formed from a hydrophilic head and a hydrophobic tail and linked together, via the hydrophilic heads, by a spacer group. Such surfactants are especially described in patent applications DE 199 43 681, DE 199 43 668, DE 42 27 391 and DE 196 08 117; JP-A-11-60437; JP-A-8-311 003; EP 0 697 244; EP 0 697 245; EP 0 708 079; DE 196 22 612 and JP-A 10-17593; WO 03/024 412; U.S. Pat. No. 5,863,886; WO 96/25388; WO 96/14926; WO 96/16930; WO 96/25384; WO 97/40124; WO 97/31890; DE 197 50 246; DE 197 50 245; DE 196 31 225; DE 196 47 060. For a detailed description of the various chemical structures and of their physicochemical properties, reference may be made to the following publications:

Milton J. Rosen, Gemini Surfactants, Properties of surfactant molecules with two hydrophilic groups and two hydrophobic groups, Cosmetics & Toiletries Magazine, vol. 113, December 1998, pages 49-55, Milton J. Rosen, Recent Developments in Gemini Surfactants, Allured's Cosmetics & Toiletries magazine, July 2001, vol. 116, No. 7, pages 67-70.

Among the above surfactant dimers are anionic surfactants corresponding to formula (I)

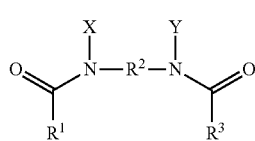

(I)

where
R$^1$ and R$^3$ represent a linear C$_8$-C$_{16}$ alkyl group,
R$^2$ represents a C$_2$-C$_8$ alkyl group,
X and Y each represent a group (C$_2$H$_4$O)$_x$—RF with x=10-15,
and RF=—SO$_3$M where M represents an alkali metal atom.

A preferred gemini surfactant of this family is a sodium dicocoylethylenediamine PEG-15 sulfate (INCI name) anionic compound of formula:

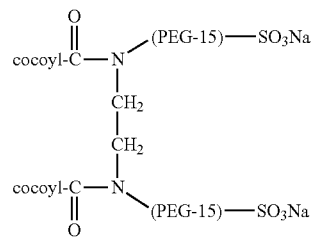

This gemini surfactant may be used, for example, in the following mixtures sold by the company Sasol under the name Ceralution®:

Ceralution® H: Behenyl Alcohol, Glyceryl Stearate, Glyceryl Stearate Citrate and Sodium Dicocoylethylenediamine PEG-15 Sulfate, Ceralution® F: Sodium Lauroyl Lactylate and Sodium Dicocoylethylenediamine PEG-15 Sulfate, Ceralution® C: Aqua, Capric/Caprylic triglyceride, Glycerin, Ceteareth-25, Sodium Dicocoylethylenediamine PEG-15 Sulfate, Sodium Lauroyl Lactylate, Behenyl Alcohol, Glyceryl Stearate, Glyceryl Stearate Citrate, Gum Arabic, Xanthan Gum, Phenoxyethanol, Methylparaben, Ethylparaben, Butylparaben, Isobutylparaben (INCI names)

The mixture Behenyl Alcohol, Glyceryl Stearate, Glyceryl Stearate Citrate et Sodium Dicocoylethylenediamine PEG-15 Sulfate (Ceralution® H) will be used more particularly.

The concentration of gemini surfactant(s) used in the present invention preferably ranges from 0.001% to 8%, preferably from 0.01% to 4% and in particular from 0.05% to 3% relative to the total weight of the photoprotective composition.

Among the other emulsion stabilizers that may be used are isophthalic acid or sulfoisophthalic acid polymers, and in particular phthalate/sulfoisophthalate/glycol copolymers, for example the diethylene glycol/phthalate/isophthalate/1,4-cyclohexanedimethanol copolymer (INCI name: Polyester-5) sold under the name Eastman AQ Polymer (AQ35S, AQ38S, AQ55S and AQ48 Ultra) by the company Eastman Chemical.

When it is an emulsion, the aqueous phase of this emulsion may comprise a nonionic vesicular dispersion prepared according to known processes (Bangham, Standish and Watkins, J. Mol. Biol. 13, 238 (1965), FR 2 315 991 and FR 2 416 008).

The compositions according to the invention find their application in a large number of treatments, especially cosmetic treatments, of the skin, the lips and the hair, including the scalp, especially for protecting and/or caring for the skin, the lips and/or the hair, and/or for making up the skin and/or the lips.

Another subject of the present invention consists of the use of the compositions according to the invention as defined above for the manufacture of cosmetic products for treating the skin, the lips, the nails, the hair, the eyelashes, the eyebrows and/or the scalp, especially care products, antisun protection products and makeup products.

The cosmetic compositions according to the invention may be used, for example, as makeup products.

The cosmetic compositions according to the invention may be used, for example, as care products and/or antisun protection products for the face and/or the body, of liquid consistency, such as milks or lotions. They may optionally be packaged to as an aerosol and may be in the form of a mousse or a spray.

According to one particularly preferred form, the compositions according to the invention may be in the form of a vaporizable fluid applied to the skin or the hair in the form of fine particles by means of pressurization devices.

According to the invention, the term "vaporizable composition" is generally intended to denote any composition that is capable of producing fine particles, under pressure in a suitable device.

The present invention also relates to a pressurization device comprising at least (A) one reservoir containing at least one vaporizable fluid composition comprising, in a cosmetically acceptable aqueous support, at least:
(a) one fatty phase;
(b) a photoprotective system capable of screening out UV radiation, as defined previously;
(c) one superabsorbent polymer as defined previously;
(d) one crosslinked copolymer of methacrylic acid and of a $C_1$-$C_4$ alkyl acrylate, and (B) means for placing the said composition under pressure.

The devices in accordance with the invention are well known to those skilled in the art and comprise non-aerosol pumps or "atomizers", one-compartment or two-compartment aerosol containers comprising a propellant and also aerosol pumps using compressed air as propellant. These devices are described in U.S. Pat. Nos. 4,077,441 and 4,850,517 (which form an integral part of the content of the description).

The compositions conditioned as one-compartment aerosols in accordance with the invention generally contain conventional propellants, for instance hydrofluoro compounds, dichlorodifluoromethane, difluoroethane, dimethyl ether, isobutane, n-butane, propane or trichlorofluoromethane. They are preferably present in amounts ranging from 15% to 50% by weight relative to the total weight of the composition.

The two-compartment aerosols are equipped with a pocket containing the composition in accordance with the invention. The propellant is located in that can and to the exterior of the pocket. It remains inside the device during use and exerts a pressure on the pocket. This propellant may be a liquefied gas such as the propellants used in one-compartment aerosols, but also a compressed gas so such as air or nitrogen.

The compositions according to the invention may also comprise additional hydrophilic or lipophilic cosmetic or dermatological active agents.

Among the active agents, mention may be made of:
vitamins (A, C, E, K, PP, and the like) and their derivatives or precursors, alone or as mixtures;
antiglycation agents;
calmatives;
NO-synthase inhibitors;
agents for stimulating the synthesis of dermal or epidermal macromolecules and/or for preventing their degradation;
agents for stimulating fibroblast proliferation;
agents for stimulating keratinocyte proliferation;
muscle relaxants;
tensioning agents;
matting agents;
keratolytic agents;
desquamating agents;
moisturizers, for instance polyols such as glycerol, butylene glycol or propylene glycol;
antiinflammatory agents;
agents that act on the energy metabolism of cells;
insect repellents;
substance P or substance CRGP antagonists;
hair-loss counteractants and/or hair restorers;
anti-wrinkle agents.

Of course, a person skilled in the art will take care to select the optional additional compound(s) and/or the amounts thereof such that the advantageous properties intrinsically associated with the compositions in accordance with the invention are not, or are not substantially, adversely affected by the envisaged addition(s).

A person skilled in the art will select the said active agent(s) as a function of the effect desired on the skin, the hair, the eyelashes, the eyebrows and the nails.

The composition may also comprise at least one ingredient such as fillers with a soft-focus effect or agents for promoting the natural coloration of the skin, intended for complementing the biological effects of these active agents or for providing an immediate visual anti-ageing effect.

For caring for and/or making up greasy skin, a person skilled in the art will preferably select at least one active agent chosen from desquamating agents, sebum-regulating agents or anti-seborrhoeic agents, and astringents.

Other Additional Ingredients

The composition may also comprise at least one additional ingredient for complementing the biological effect of these active agents or for affording an so immediate visual effect; mention may be made especially of matting agents, soft-focus fillers, fluorescers, agents for promoting the naturally pinkish coloration of the skin, and abrasive fillers or exfoliants.

To complement and/or optimize the effects imparted by the cosmetic and/or dermatological active agents mentioned above on the keratin materials, it may be advantageous to incorporate into the compositions of the invention other additional ingredients.

In particular, these additional ingredients may impart an immediate visual effect to that will be relayed by the biological effect of the active agents mentioned above.

They may also, via a mechanical action (e.g.: abrasive fillers), amplify the effect of the biological active agents mentioned above.

Matting Agents

The term "matting agent" means agents intended to make the skin visibly more matt and less shiny.

The matting effect of the agent and/or composition containing it may especially be evaluated using a gonioreflectometer, by measuring the ratio R between the specular reflection and the scattered reflection. A value of R of less than or equal to 2 generally indicates a matting effect.

The matting agent may especially be chosen from a rice starch or a corn starch: INCI name: Zea mays (Corn) Starch, such as, in particular, the product sold under the trade name Farmal CS 3650 Plus 036500 by National Starch, kaolinite, talc, a pumpkin seed extract, cellulose microbeads, plant fibres, synthetic fibres, in particular polyamide fibres, expanded acrylic copolymer microspheres, polyamide powders, silica powders, polytetrafluoroethylene powders, silicone resin powders, acrylic polymer powders, wax powders, polyethylene powders, powders of elastomeric crosslinked organopolysiloxane coated with silicone resin, talc/titanium dioxide/alumina/silica composite powders, amorphous mixed silicate powders, silicate particles and especially mixed silicate particles, and mixtures thereof.

Examples of matting agents that may especially be mentioned include:
rice or corn starch, in particular an aluminium starch octenyl succinate sold under the name Dry Flo® by the company National Starch;
kaolinite;
silicas;
talc;
a pumpkin seed extract as sold under the name Curbilene® by the company Indena;
cellulose microbeads as described in patent application EP 1 562 562;
fibres, such as silk fibre, cotton fibre, wool fibre, flax fibre, cellulose fibre extracted especially from wood, from vegetables or from algae, polyamide fibre (Nylon®), modified cellulose fibre, poly-p-phenyleneterephthamide fibre, acrylic fibre, polyolefin fibre, glass fibre, silica fibre, aramid fibre, carbon fibre, Teflon® fibre, insoluble collagen fibre, polyester fibre, polyvinyl chloride or polyvinylidene chloride fibre, polyvinyl alcohol fibre, polyacrylonitrile fibre, chitosan fibre, so polyurethane fibre, polyethylene phthalate fibre, fibres formed from a mixture of polymers, resorbable synthetic fibres, and mixtures thereof described in patent application EP 1 151 742;
expanded acrylic copolymer microspheres such as those sold by the company Expancel under the name Expancel 551®;
fillers with an optical effect as described in patent application FR 2 869 796, in particular:
polyamide powders (Nylon®), for instance Nylon 12 particles of the Orgasol type from Arkema, with a mean size of 10 microns and a refractive index of 1.54,
silica powders, for instance Silica beads SB150 from Miyoshi with a mean size of 5 microns and a refractive index of 1.45,
polytetrafluoroethylene powders, for instance PTFE Ceridust 9205F from Clariant, with a mean size of 8 microns and a refractive index of 1.36,
silicone resin powders, for instance the silicone resin Tospeari 145A from GE Silicone with a mean size of 4.5 microns and a refractive index of 1.41,
acrylic copolymer powders, especially of polymethyl (meth)acrylate, for instance the PMMA particles Jurymer MBI from Nihon Junyoki, with a mean size of 8 microns and a refractive index of 1.49, or the Micropearl M100® and F 80 ED® particles from the company Matsumoto Yushi-Seiyaku,
wax powders, for instance the paraffin wax particles Microease 114S from Micropowders, with a mean size of 7 microns and a refractive index of 1.54,
polyethylene powders, especially comprising at least one ethylene/acrylic acid copolymer, and in particular consisting of ethylene/acrylic acid copolymers, for instance the particles Flobeads EA 209 from Sumitomo (with a mean size of 10 microns and a refractive index of 1.48),
elastomeric crosslinked organopolysiloxane powders coated with silicone resin, especially with silsesquioxane resin, as described, for example, in U.S. Pat. No. 5,538,793. Such elastomer powders are sold under the names KSP-100. KSP-101, KSP-102, KSP-103, KSP-104 and KSP-105 by the company Shin-Etsu, and
talc/titanium dioxide/alumina/silica composite powders such as those sold under the name Coverleaf® AR-80 by the company Catalyst & Chemicals,
mixtures thereof,
compounds that absorb and/or adsorb sebum as described in patent application FR 2 869 796. Mention may be made especially of:
silica powders, for instance the porous silica microspheres sold under the name Silica Beads SB-700 sold by the company Miyoshi, the products Sunsphere® H51, Sunsphere® H33 and Sunsphere® H53 sold by the company Asahi Glass; the polydimethylsiloxane-coated amorphous silica microspheres sold under the name SA Sunsphere® H-33 and SA Sunsphere® H-53 sold by the company Asahi Glass;
amorphous mixed silicate powders, especially of aluminium and magnesium, for instance the product sold under the name Neusilin UFL2 by the company Sumitomo;
polyamide (Nylon®) powders, for instance Orgasol® 4000 sold by the company Arkema, and
acrylic polymer powders, especially of polymethyl methacrylate, for instance Covabead® LH85 sold by the company Wackherr, of polymethyl methacrylate/ethylene glycol dimethacrylate, for instance Dow Corning 5640 Microsponge® Skin Oil Adsorber sold by the company Dow Corning, or so Ganzpearl® GMP-0820 sold by the company Ganz Chemical; of polyallyl methacrylate/ethylene glycol dimethacrylate, for instance Poly-Pore® L200 or Poly-Pore® E200 sold by the company Amcol; of ethylene glycol dimethacrylate/lauryl methacrylate copolymer, for instance Polytrap® 6603 sold by the company Dow Corning;
silicate particles, such as alumina silicate;
mixed silicate particles, such as:
magnesium aluminium silicate particles, such as saponite or hydrated magnesium aluminium silicate with a sodium sulfate sold under the trade name Sumecton® by the company Kunimine;
the magnesium silicate, hydroxyethylcellulose, black cumin oil, marrow oil and phospholipids complex or Matipure® from Lucas Meyer, and
mixtures thereof.

Preferred matting agents that may be used according to the invention include a pumpkin seed extract, a rice or corn starch, kaolinite, silicas, talc, polyamide powders, polyethylene powders, acrylic copolymer powders, expanded acrylic copolymer microspheres, silicone resin microbeads and mixed silicate particles, and mixtures thereof.

Fillers with a Soft-focus Effect

These fillers may be any material capable of modifying and hiding wrinkles by virtue of their intrinsic physical properties. These fillers may especially modify wrinkles via a tensioning effect, a covering effect or a soft-focus effect.

Examples of fillers that may be given include the following compounds:
porous silica microparticles, for instance the Silica Beads® SB150 and SB700 from Miyoshi with a mean size of 5 µm; the series H Sunspheres® from Asahi Glass, for instance Sunspheres H33, H51 with respective sizes of 3.5 and 5 µm;
hollow hemispherical silicone resin particles such as NLK 500®, NLK 506® and NLK 510® from Takemoto Oil and Fat, especially described in EP-A-1 579 849;

silicone resin powders, for instance the silicone resin Tospearl® 145A from GE Silicone, with a mean size of 4.5 μm;

acrylic copolymer powders, especially of polymethyl (meth)acrylate, for instance the PMMA particles Jurymer MBI® from Nihon Junyoki, with a mean size of 8 μm, the hollow PMMA spheres sold under the name Covabead® LH85 by the company Wackherr, and vinylidene/acrylonitrile/methylene methacrylate expanded microspheres sold under the name Expancel®;

wax powders, for instance the paraffin wax particles MicroEase® 114S from MicroPowders, with a mean size of 7 μm;

polyethylene powders, especially comprising at least one ethylene/acrylic acid copolymer, for instance the Flobeads® EA 209 E particles from Sumitomo, with a mean size of 10 μm;

crosslinked elastomeric organopolysiloxane powders coated with silicone resin and especially with silsesquioxane resin, under the names KSP-100®, KSP-101®, KSP-102®, KSP-103®, KSP-104® and KSP-105® by the company Shin-Etsu;

talc/titanium dioxide/alumina/silica composite powders, for instance those sold under the name Coverleaf AR-80® by the company Catalyst & Chemicals;

talc, mica, kaolin, lauryl glycine, starch powders crosslinked with octenyl so succinate anhydride, boron nitride, polytetrafluoroethylene powders, precipitated calcium carbonate, magnesium carbonate, magnesium hydrogen carbonate, barium sulfate, hydroxyapatite, calcium silicate, cerium dioxide and glass or ceramic microcapsules;

hydrophilic or hydrophobic, synthetic or natural, mineral or organic fibres such as silk fibres, cotton fibres, wool fibres, flax fibres, cellulose fibres extracted especially from wood, vegetables or algae, polyamide (Nylon®) fibres, modified cellulose fibres, poly-p-terephthamide fibres, acrylic fibres, polyolefin fibres, glass fibres, silica fibres, aramid fibres, carbon fibres, polytetrafluoroethylene (Teflon®) fibres, insoluble collagen fibres, polyester fibres, polyvinyl chloride fibres, polyvinylidene chloride fibres, polyvinyl alcohol fibres, polyacrylonitrile fibres, chitosan fibres, polyurethane fibres, polyethylene phthalate fibres, fibres formed from a mixture of polymers, resorbable synthetic fibres, and mixtures thereof described in patent application EP 1 151 742;

spherical elastomeric crosslinked silicones, for instance Trefil E-505C® or E-506C® from Dow Corning;

abrasive fillers, which, via a mechanical effect, smooth out the skin microrelief, such as abrasive silica, for instance Abrasif SP® from Semanez or nutshell powders (for example of apricot or walnut, from Cosmetochem).

The fillers with an effect on the signs of ageing are especially chosen from porous silica microparticles, hollow hemispherical silicone particles, silicone resin powders, acrylic copolymer powders, polyethylene powders, crosslinked elastomeric organopolysiloxane powders coated with silicone resin, talc/titanium dioxide/alumina/silica composite powders, precipitated calcium carbonate, magnesium carbonate, magnesium hydrogen carbonate, barium sulfate, hydroxyapatite, calcium silicate, cerium dioxide, glass or ceramic microcapsules, and silk fibres or cotton fibres, and mixtures thereof.

The filler may be a soft-focus filler.

The term "soft-focus" filler means a filler which in addition gives the complexion transparency and a hazy effect. Preferably, the soft-focus fillers have a mean particle size of less than or equal to 15 microns. These particles may be in any form and in particular may be spherical or non-spherical. These fillers are more preferably non-spherical.

The soft-focus fillers may be chosen from silica and silicate powders, especially alumina powder, powders of polymethyl methacrylate (PMMA) type, talc, silica/TiO2 or silica/zinc oxide composites, polyethylene powders, starch powders, polyamide powders, styrene/acrylic copolymer powders and silicone elastomers, and mixtures thereof.

Mention may be made in particular of talc with a number-average size of less than or equal to 3 microns, for example talc with a number-average size of 1.8 microns and especially the product sold under the trade name Talc P3® by the company Nippon Talc, Nylon® 12 powder, especially the product sold under the name Orgasol 2002 Extra D Nat Cos® by the company Atochem, silica particles 1% to 2% surface-treated with a mineral wax (INCI name: hydrated silica (and) paraffin) such as the products sold by the company Degussa, amorphous silica microspheres, such as the products sold under the name Sunsphere, for example so of reference H-53® by the company Asahi Glass, and silica microbeads such as those sold under the name SB-700® or SB-150® by the company Miyoshi, this list not being limiting.

The concentration of these fillers with an effect on the signs of ageing in the compositions according to the invention may be between 0.1% and 40%, or even between 0.1% and 20% by weight, relative to the total weight of the composition.

Agents for Promoting the Naturally Pinkish Coloration of the Skin

Mention may be made especially of:

a self-tanning agent, i.e. an agent which, when applied to the skin, especially to the face, can produce a tan effect that is more or less similar in appearance to that which may result from prolonged exposure to the sun (natural tan) or under a UV lamp;

an additional colouring agent, i.e. any compound that has particular affinity for the skin, which allows it to give the skin a lasting, non-covering coloration (i.e. that does not have a tendency to opacify the skin) and that is not removed either with water or using a solvent, and that withstands both rubbing and washing with a solution containing surfactants. Such a lasting coloration is thus distinguished from the superficial and transient coloration provided, for example, by a makeup pigment;

and mixtures thereof.

Examples of self-tanning agents that may especially be mentioned include:

dihydroxyacetone (DHA), erythrulose, and the combination of a catalytic system formed from:

manganese and/or zinc oxide salts, and alkali metal and/or alkaline-earth metal hydrogen carbonates.

The self-tanning agents are generally chosen from monocarbonyl or polycarbonyl compounds, for instance isatin, alloxan, ninhydrin, glyceraldehyde, mesotartaric aldehyde, glutaraldehyde, erythrulose, pyrazolin-4,5-dione derivatives as described in patent application FR 2 466 492 and WO 97/35842, dihydroxyacetone (DHA) and 4,4-dihydroxypyrazolin-5-one derivatives as described in patent application EP 903 342. DHA will preferably be used.

DHA may be used in free and/or encapsulated form, for example in lipid vesicles such as liposomes, especially described in patent application WO 97/25970.

In general, the self-tanning agent is present in an amount ranging from 0.01% to 20% by weight and preferably in an amount of between 0.1% and 10% of the total weight of the composition.

Other dyes that allow modification of the colour produced by the self-tanning agent may also be used.

These dyes may be chosen from synthetic or natural direct dyes.

These dyes may be chosen, for example, from red or orange dyes of the fluorane type such as those described in patent application FR 2 840 806. Mention may be made, for example, of the following dyes:

tetrabromofluorescein or eosin known under the CTFA name: CI 45380 or Red 21 phloxin B known under the CTFA name: CI 45410 or Red 27 diiodofluorescein known under the CTFA name: CI 45425 or Orange 10;

dibromofluorescein known under the CTFA name: CI 45370 or Orange 5;

the sodium salt of tetrabromofluorescein known under the CTFA name: CI 45380 to (Na salt) or Red 22;

the sodium salt of phloxin B known under the CTFA name: CI 45410 (Na salt) or Red 28;

the sodium salt of diiodofluorescein known under the CTFA name: CI 45425 (Na salt) or Orange 11;

erythrosine known under the CTFA name: CI 45430 or Acid Red 51.

phloxin known under the CTFA name: CI 45405 or Acid Red 98.

These dyes may also be chosen from anthraquinones, caramel, carmine, carbon black, azulene blues, methoxalene, trioxalene, guajazulene, chamuzulene, rose Bengal, eosin 10B, cyanosin and daphinin.

These dyes may also be chosen from indole derivatives, for instance the monohydroxyindoles as described in patent FR 2 651 126 (i.e.: 4-, 5-, 6- or 7-hydroxyindole) or the dihydroxyindoles as described in patent EP-B-0 425 324 (i.e.: 5,6-dihydroxyindole, 2-methyl-5,6-dihydroxyindole, 3-methyl-5,6-dihydroxyindole or 2,3-dimethyl-5,6-dihydroxyindole).

Abrasive Fillers or Exfoliants

As exfoliants that may be used in rinse-out compositions according to the invention, examples that may be mentioned include exfoliant or scrubbing particles of mineral, plant or organic origin. Thus, polyethylene beads or powder, Nylon powder, polyvinyl chloride powder, pumice powder, ground apricot kernel or walnut husk, sawdust, glass beads and alumina, and mixtures thereof, may be used, for example. Mention may also be made of Exfogreen® from Solabia (bamboo extract), extracts of strawberry akenes (Strawberry Akenes from Greentech), peach kernel powder, apricot kernel powder, and finally, in the field of plant powders with an abrasive effect, mention may be made of cranberry kernel powder.

As abrasive fillers or exfoliants that are preferred according to the invention, mention will be made of peach kernel powder, apricot kernel powder, cranberry kernel powder, strawberry akene extracts and bamboo extracts.

The examples that follow serve to illustrate the invention without, however, being limiting in nature. In these examples, the amounts of the composition ingredients are given as weight percentages relative to the total weight of the composition.

EXAMPLES 1 to 7

Fluid antisun formulations 1 to 7 below were prepared. All the formulae are O/W emulsions having the following common support:

| Phase | Ingredients | weight % |
|---|---|---|
| A | Water | qs 100 |
|  | Preserving agents | 1.5 |
|  | Glycerol | 15.0 |
|  | Butylene glycol | 2.0 |
|  | Terephthalylidenedicamphorsulfonic acid (Mexoryl SX) | 0.4 |
|  | Triethanolamine | 0.11 |
|  | Dye | 0.001 |
| B | Behenyl Alcohol (and) Glyceryl Stearate (and) Disodium Ethylene Dicocamide PEG-15 Disulfate (and) Glyceryl Stearate Citrate (Ceralution H) | 1.5 |
|  | Butylmethoxydibenzoylmethane | 4.0 |
|  | Octyl salicylate | 5.0 |
|  | Octocrylene | 7.0 |
|  | Ethylhexyl triazone | 1.6 |
|  | Drometrizole trisiloxane | 0.6 |
|  | Titanium Dioxide (and) Aluminum Hydroxide (and) Stearic Acid | 1.5 |
|  | Fragrance | 0.6 |
|  | Vitamin E | 0.1 |
|  | Dimethicone | 1.0 |
| C | Sodium Acrylates Crosspolymer-2 (and) Aqua (and) Silica (Aquakeep 10SH.NF) | 0.7 |
| D | Gelling agent | 0 to 0.5 |
|  | Triethanolamine | qs |
| E | Denatured ethanol | 7.0 |

Procedure for the Composition (in a COS1000—Esco Labor Tank)

Phase B is melted with paddle and doctor blade stirring at 75° C. and then cooled to 65° C. Phase A is prepared with stirring at 65° C. with only part of the water. The emulsification is performed: phase A is poured slowly into phase B with turbomixing, and is turbomixed for 10 minutes using paddles and doctor blades. Phase C is added and the whole is turbomixed for 5 minutes using paddles and doctor blades. Phase D (gelling agent only) is added and the whole is turbomixed for 5 minutes using paddles and doctor blades. The rest of the water of phase A is added and the whole is turbomixed for 5 minutes using paddles and doctor blades. Phase D (triethanolamine) is added and the whole is turbomixed for 5 minutes using paddles and doctor blades, and is then cooled to room temperature. Phase E is added at room temperature, and the whole is turbomixed for 5 minutes using paddles and doctor blades.

Example 1: no gelling agent

Example 2: 0.35% poly(2-acrylamido-2-methylpropanesulfonic acid) sold by the company Hoechst under the trade name Hostacerin AMPS Example 3: 0.5% Hostacerin AMPS Example 4: 0.15% methacrylic acid/ethyl acrylate cross-linked copolymer in aqueous dispersion (Carbopol Aqua SF1)

Example 5: 0.2% Hostacerin AMPS/0.2% xanthan gum combination

Example 6: 0.2% Hostacerin AMPS/0.15% acrylate/$C_{10}$-$C_{30}$-alkylacrylate copolymer combination (Pemulen TR1)

Example 7: 0.2% Hostacerin AMPS/0.15% methacrylic acid/ethyl acrylate crosslinked copolymer in aqueous dispersion (Carbopol Aqua SF1) combination The viscosity is measured and the appearance of each formula at 24 hours and its stability after 2 months at 45° C. are observed.

A formula is described as being "unstable" when it shows instability in the accelerated stability tests (2 months, 45° C.). This instability is reflected by the presence of instability (draining out, phase separation or substantial deposit at the bottom of the tube) during the centrifugation test for 30 minutes at 900×g.

Results:

The use of a standard gelling agent, even when its content is increased, does not make it possible to stabilize the formulae with the superabsorbent polymer Aquakeep while maintaining the fluidity.

Only the methacrylic acid/ethyl acrylate crosslinked copolymer (Carbopol Aqua to SF1) combined with the absorbent polymer makes it possible to stabilize formula 4 while conserving its fluidity.

EXAMPLES 8 AND 9

Fluid antisun formulations 8 and 9 below were prepared. All the formulae are O/W emulsions having the following common support:

TABLE 1

|  | Example 1 (outside the invention) | Example 2 (outside the invention) | Example 3 (outside the invention) | Example 4 (invention) |
| --- | --- | --- | --- | --- |
| Appearance | Non-uniform fluid milk | Fluid milk Non-uniform | Thick milk | Fluid milk |
| Stability | Multiple phase separation and titanium deposit on centrifugation, unstable after 2 months at 45° C. | Phase separation and titanium deposit on centrifugation, unstable after 2 months at 45° C. | Graining out and titanium deposit on centrifugation, unstable after 2 months at 45° C. | Centrifugation compliant, stable after 2 months at 45° C. |
| Viscosity 10 minutes in Pa · s | 0.23 | 1.03 | 1.53 | 0.27 |
| Gelling agents used | Absence of gelling agent | Hostacerin AMPS 0.35% | Hostacerin AMPS 0.5% | 0.15% methacrylic acid/ethyl acrylate crosslinked copolymer in aqueous dispersion (Carbopol Aqua SF1) |

TABLE 2

|  | Example 5: (outside the invention) | Example 6: (outside the invention) | Example 7: (invention) |
| --- | --- | --- | --- |
| Appearance | Milk | Very thick milk with slight greasiness | Milk |
| Stability | Substantial phase separation on centrifugation, unstable at 2 months at 45° C. | Graining out on centrifugation, unstable after 2 months at 45° C. | Centrifugation compliant, stable after 2 months at 45° C. |
| Viscosity 10 minutes in Pa · s | 1.15 | 2.03 | 1.32 |
| Gelling agents | Hostacerin AMPS 0.2% Xanthan gum 0.2% | Hostacerin AMPS 0.2% PEMULEN TR1 0.15% | Hostacerin AMPS 0.2% 0.15% methacrylic acid/ethyl acrylate crosslinked copolymer in aqueous dispersion (Carbopol Aqua SF1) 0.15% |

| Phase | Ingredients | % |
|---|---|---|
| A | Water | qs 100 |
|  | Preserving agents | 1.5 |
|  | Glycerol | 15.0 |
|  | Butylene glycol | 2.0 |
|  | Terephthalylidenedicamphorsulfonic acid (Mexoryl SX) | 0.4 |
|  | Triethanolamine | 0.11 |
|  | Colorant CI42090 | 0.00045 |
| B | Inulin Lauryl Carbamate | 0.3 |
|  | Butylmethoxydibenzoylmethane | 4.0 |
|  | Octyl salicylate | 5.0 |
|  | Octocrylene | 7.0 |
|  | Ethylhexyl triazone | 1.6 |
|  | Drometrizole trisiloxane | 0.6 |
|  | Titanium Dioxide (and) Aluminum Hydroxide (and) Stearic Acid | 1.5 |
|  | Fragrance | 0.6 |
|  | Vitamin E | 0.1 |
|  | Dimethicone | 1.0 |
|  | Synthetic Wax | 1.0 |
| C | Sodium Acrylates Crosspolymer-2 (and) Aqua (and) Silica (Aquakeep) | 0.7 |
| D | Gelling agent | 0.35 or 0.4 |
|  | Triethanolamine | qs |
| E | Denatured ethanol | 5.0 |

The procedure is identical to that described in Examples 1 to 7.

Example 8: 0.2% Hostacerin AMPS/0.2% xanthan gum combination

Example 9: 0.2% Hostacerin AMPS/0.5% methacrylic acid/ethyl acrylate crosslinked copolymer in aqueous dispersion (Carbopol Aqua SF1) combination The viscosity is measured and the appearance of each formula at 24 hours and its stability after 2 months at 45° C. are observed.

A formula is described as being "unstable" when it shows instability in the accelerated stability tests (2 months, 45° C.). This instability is reflected by the presence of instability (draining out, phase separation or substantial deposit at the bottom of the tube) during the centrifugation test for 30 minutes at 900×g.

Results:

TABLE 3

|  | Example 8 (outside the invention) | Example 9: (invention) |
|---|---|---|
| Appearance | Marbled milk | Marbled milk |
| Stability | Titanium deposit, little graining out, non-uniform blue-white tube on centrifugation, unstable after 2 months at 45° C. | Nothing to report and on centrifugation, stable after 2 months at 45° C. |
| Viscosity at 10 minutes in Pa · s | 1.61 | 1.45 |
| Gelling agents | Hostacerin AMPS 0.2% Xanthan gum 0.2% | Hostacerin AMPS 0.2% methaciylic acid/ethyl acrylate crosslinked copolymer in aqueous dispersion (Carbopol Aqua SF1) 0.15% |

The use of a standard gelling agent, even when its content is increased, does not make it possible to stabilize the formulae with the superabsorbent polymer while maintaining the fluidity.

Only the methacrylic acid/ethyl acrylate crosslinked copolymer (Carbopol Aqua SF1) combined with the absorbent polymer makes it possible to stabilize formula 9 based on inulin lauryl carbamate while conserving its fluidity.

EXAMPLE 10

Demonstration of the Freshness Effect Obtained with the Combination of Polymers of the Invention The sensory properties of the following two formulae are evaluated by a panel of 11 people:

| Phase | Ingredients | Ex. 7 (outside the invention) | Ex. 10 (invention) |
|---|---|---|---|
| A | Water | qs 100 | qs 100 |
|  | Preserving agents | 1.5 | 1.5 |
|  | Glycerol | 15.0 | 15.0 |
|  | Butylene glycol | 2.0 | 2.0 |
|  | Terephthalylidenedicamphorsulfonic acid (Mexoryl SX) | 0.4 | 0.4 |
|  | Triethanolamine | 0.11 | 0.11 |
|  | Dye | 0.001 | 0.001 |
| B | Behenyl Alcohol (and) Glyceryl Stearate (and) Disodium Ethylene Dicosamide PEG-15 Disuifate (and) Glyceryl Stearate Citrate (Ceralution H) | 1.5 | 1.5 |
|  | Butylmethoxydibenzoylmethane | 4.0 | 4.0 |
|  | Octyl salicylate | 5.0 | 5.0 |
|  | Octocrylene | 7.0 | 7.0 |
|  | Ethylhexyl triazone | 1.6 | 1.6 |
|  | Drometrizole trisiloxane | 0.6 | 0.6 |
|  | Titanium Dioxide (and) Aluminum Hydroxide (and) Stearic Acid | 1.5 | 1.5 |
|  | Fragrance | 0.6 | 0.6 |
|  | Vitamin E | 0.1 | 0.1 |
|  | Dimethicone | 1.0 | 1.0 |
| C | Sodium Acrylates Crosspolymer-2 (and) Aqua (and) Silica (Aquakeep) | — | 0.7 |
| D | Hostacerin AMPS | 0.2 | 0.2 |
|  | Methacrylic acid/ethyl acrylate crosslinked copolymer in aqueous dispersion (Carbopol Aqua SF1) | 0.15 | 0.15 |
|  | Triethanolamine | 0.125 | 0.125 |
| E | Denatured ethanol | 7.0 | 7.0 |

Results

Formula 10 according to the invention with the superabsorbent polymer/methacrylic acid/ethyl acrylate crosslinked copolymer is significantly preferred:
- 8 out of 11 people considered that formula 10 was fresher on application;
- 7 out of 11 people considered that formula 10 had more persistent freshness;
- 6 out of 11 people considered that formula 10 was easier and more pleasant to spread.

The invention claimed is:

1. A fluid composition, which comprises, in a cosmetically acceptable aqueous support:
   (a) at least one fatty phase;
   (b) a photoprotective system capable of screening out UV radiation;
   (c) at least one superabsorbent polymer, wherein the superabsorbent polymer is present in an active material content ranging from 0.1% to 2% by weight relative to the total weight of the composition; and
   (d) at least one crosslinked copolymer of methacrylic acid and of a $C_1$-$C_4$ alkyl acrylate, wherein the crosslinked copolymer of methacrylic acid and of an alkyl acrylate is present in amounts ranging from 0.01% to 1% by weight of active material relative to the total weight of the composition.

2. The fluid composition according to claim 1, wherein the superabsorbent polymer is in the form of particles with a number-average diameter ranging from 10 μm to 1000 μm.

3. The fluid composition according to claim 1, wherein the superabsorbent polymer is in the form of particles with a number-average diameter of less than or equal to 100 μm.

4. The fluid composition according to claim 1, wherein the superabsorbent polymer has a water-absorbing capacity from 10 to 100 g/g.

5. The fluid composition according to claim 1, wherein the superabsorbent polymer is chosen from crosslinked sodium polyacrylates, starches grafted with an acrylic polymer, hydrolysed starches grafted with an acrylic polymer, and polymers based on starch, gum and cellulose derivatives, and mixtures thereof.

6. The fluid composition according to claim 1, wherein the superabsorbent polymer is chosen from crosslinked sodium polyacrylates.

7. The fluid composition according to claim 1, wherein, in the crosslinked copolymer of methacrylic acid and of a $C_1$-$C_4$ alkyl acrylate:
(i) methacrylic acid is present in amounts ranging from 20% to 80% by relative to the total weight of the copolymer,
(ii) the alkyl acrylate is present in amounts ranging from 15% to 80% by weight relative to the total weight of the copolymer.

8. The fluid composition according to claim 1, wherein, in the crosslinked copolymer of methacrylic acid and of a $C_1$-$C_4$ alkyl acrylate is in the form of a dispersion in water.

9. The fluid composition according to claim 8, wherein the mean size of the copolymer particle in the dispersion is generally between 10 and 500 nm.

10. The fluid composition according to claim 1, wherein the crosslinked copolymer of methacrylic acid and of a $C_1$-$C_4$ an alkyl acrylate is a crosslinked copolymer of methacrylic acid and of ethyl acrylate.

11. The fluid composition according to claim 1, which is in the form of an oil-in-water or water-in-oil emulsion.

12. The fluid composition according to claim 11, which comprises at least one emulsifier chosen from hydrophobic modified inulins.

13. The fluid composition according to claim 11, which comprises at least one emulsifier chosen from surfactant dimers comprising two identical or different surfactant units, each formed from a hydrophilic head and a hydrophobic tail and linked together, via the hydrophilic heads, with a spacer group.

14. The fluid composition according to claim 1 the superabsorbent polymer and crosslinked copolymer of methacrylic acid and of an alkyl acrylate, in the fluid composition comprising, in the cosmetically acceptable aqueous support, and the at least one photoprotective system capable of screening out UV radiation, are present as a freshness agent and/or as a stabilizer for the composition.

15. The fluid composition according to claim 1, wherein the superabsorbent polymer is in the form of particles with a number-average diameter of less than or equal to 50 μm.

16. The fluid composition according to claim 1, wherein the superabsorbent polymer has a water-absorbing capacity from 20 to 80 g/g.

17. The fluid composition according to claim 1, wherein the superabsorbent polymer is an acryloacrylamide/sodium acrylate copolymer.

18. The fluid composition according to claim 1, wherein the superabsorbent polymer is present in an active material content ranging from 0.5% to 1.5% by weight relative to the total weight of the composition.

19. The fluid composition according to claim 1, wherein the crosslinked copolymer of methacrylic acid and of a $C_1$-$C_4$ alkyl acrylate is crosslinked with at least one polyethylenically unsaturated crosslinking agent selected from the group consisting of polyalkenyl ethers of sucrose, polyalkenyl ethers of polyols, diallyl phthalates, divinylbenzene, allyl (meth)acrylate, ethylene glycol di(meth)acrylate, methylenebisacrylamide, trimethylolpropane tri(meth)acrylate, diallyl itaconate, diallyl fumarate, diallyl maleate, zinc (meth)acrylate, castor oil and polyol derivatives of unsaturated carboxylic acids, in an amount from 0.01% to 5% by weight relative to the total weight of the crosslinked copolymer.

20. The fluid composition according to claim 1, wherein the crosslinked copolymer of methacrylic acid and of a $C_1$-$C_4$ alkyl acrylate is a crosslinked copolymer of methacrylic acid ethyl acrylate.

\* \* \* \* \*